(12) United States Patent
Wilzbach et al.

(10) Patent No.: US 10,736,503 B2
(45) Date of Patent: *Aug. 11, 2020

(54) METHOD, OPHTHALMIC MEASURING SYSTEMS AND COMPUTER-READABLE STORAGE MEDIUM FOR SELECTING AN INTRAOCULAR LENS

(71) Applicant: CARL ZEISS MEDITEC AG, Jena (DE)

(72) Inventors: Marco Wilzbach, Stuttgart (DE); Christoph Hauger, Aalen (DE); Markus Seesselberg, Aalen (DE); Xing Wei, Dublin, CA (US); Holger Matz, Unterschneidheim (DE); Anja Seiwert, Aalen (DE); Oliver Findl, Vienna (AT); Nino Hirnschall, Vienna (AT)

(73) Assignee: CARL ZEISS MEDITEC AG, Jena (DE)

( * ) Notice: Subject to any disclaimer, the term of this patent is extended or adjusted under 35 U.S.C. 154(b) by 90 days.

This patent is subject to a terminal disclaimer.

(21) Appl. No.: 16/034,462

(22) Filed: Jul. 13, 2018

(65) Prior Publication Data
US 2018/0317765 A1 Nov. 8, 2018

Related U.S. Application Data

(63) Continuation of application No. 13/871,301, filed on Apr. 26, 2013, now Pat. No. 10,117,572.

(51) Int. Cl.
*A61B 3/10* (2006.01)
*A61B 3/00* (2006.01)
*A61F 2/16* (2006.01)

(52) U.S. Cl.
CPC ............ *A61B 3/102* (2013.01); *A61B 3/0025* (2013.01); *A61F 2/16* (2013.01); *A61F 2240/002* (2013.01)

(58) Field of Classification Search
CPC ..... A61B 3/102; A61B 3/1005; A61B 5/0066; A61B 3/0025; A61B 3/10; A61B 5/0073;
(Continued)

(56) References Cited

U.S. PATENT DOCUMENTS

| 4,710,193 A | 12/1987 | Volk |
| 5,968,095 A | 10/1999 | Norrby |

(Continued)

FOREIGN PATENT DOCUMENTS

| DE | 102010010569 A1 | 9/2011 |
| WO | 2006053216 A2 | 5/2006 |

(Continued)

OTHER PUBLICATIONS

Association for Research in Vision and Ophthalmology. ARVO 2012 Annual Meeting. May 6-9, 2012. http:!/web.archive.org/web/20120720202501/http://www.arvo.org/Annual_Meeting/2012/Program.

(Continued)

*Primary Examiner* — Collin X Beatty
(74) *Attorney, Agent, or Firm* — Patent Portfolio Builders, PLLC

(57) ABSTRACT

A method of determining at least one selection parameter for selecting an intraocular lens to be inserted into an eye; the method comprises reading, by a data processing system, data indicative of an axial position of at least a portion of an anterior surface of an at least partially empty capsular bag of the eye, relative to an optical axis of the eye. The method further comprises determining an axial position parameter, which is representative of the axial position of the portion of the anterior surface, depending on the data. The method further comprises determining the at least one selection parameter for selecting the intraocular lens depending on the determined position parameter.

10 Claims, 7 Drawing Sheets

(58) Field of Classification Search
CPC ....... A61B 3/117; G01B 9/02091; A61F 2/16;
A61F 2009/00851; A61F 2009/0087;
A61F 2009/00872; A61F 2009/00887;
A61F 2009/00889; A61F 9/00736; A61F
2009/00853; A61F 2/1602; G06T
2207/30041; G06T 2207/10101; B29D
11/023
USPC ............... 351/246, 205, 159.77; 128/898;
600/558; 623/6.11, 905
See application file for complete search history.

(56) References Cited

U.S. PATENT DOCUMENTS

| | | | |
|---|---|---|---|
| 6,419,359 | B2 | 7/2002 | Edwards |
| 6,626,538 | B1 | 9/2003 | Arrowsmith |
| 6,663,240 | B2 | 12/2003 | Patel |
| 6,695,880 | B1 | 2/2004 | Roffman et al. |
| 6,905,641 | B2 | 6/2005 | Platt et al. |
| 7,044,604 | B1 | 5/2006 | Arrowsmith |
| 7,322,699 | B2 | 1/2008 | Barth et al. |
| 7,556,378 | B1 | 7/2009 | Ianchulev |
| 7,988,291 | B2 | 8/2011 | Ianchulev |
| 7,993,398 | B2 | 8/2011 | Deacon et al. |
| 8,002,827 | B2 | 8/2011 | Deacon et al. |
| 8,128,228 | B2 | 3/2012 | Van Heugten |
| 8,231,672 | B2 | 7/2012 | Deacon et al. |
| 8,241,353 | B2 | 8/2012 | Deacon et al. |
| 8,313,196 | B2 | 11/2012 | Ianchulev |
| 8,556,421 | B2 | 10/2013 | Simpson |
| 8,632,178 | B2 | 1/2014 | Simpson |
| 2004/0054358 | A1 | 3/2004 | Cox et al. |
| 2006/0235369 | A1 | 10/2006 | MacRae et al. |
| 2007/0010730 | A1 | 1/2007 | Gordon |
| 2007/0073905 | A1 | 3/2007 | Cynthia et al. |
| 2007/0260157 | A1 | 11/2007 | Norrby |
| 2009/0164007 | A1 | 6/2009 | Heugten |
| 2009/0251664 | A1 | 10/2009 | Norrby et al. |
| 2010/0082017 | A1 | 4/2010 | Zickler et al. |
| 2010/0130888 | A1 | 5/2010 | Deacon et al. |
| 2010/0134763 | A1 | 6/2010 | Bünau et al. |
| 2010/0277691 | A1 | 11/2010 | Huang et al. |
| 2010/0302550 | A1 | 12/2010 | Hacker et al. |
| 2010/0331830 | A1 | 12/2010 | Bischoff et al. |
| 2011/0013141 | A1* | 1/2011 | Holladay ............ A61B 3/1005 351/221 |
| 2011/0015541 | A1 | 1/2011 | Padrick et al. |
| 2011/0051083 | A1 | 3/2011 | Geggel |
| 2011/0052020 | A1 | 3/2011 | Hildebrand et al. |
| 2011/0128502 | A1 | 6/2011 | Norrby et al. |
| 2011/0199577 | A1 | 8/2011 | Wilzbach et al. |
| 2011/0208172 | A1 | 8/2011 | Youssefi et al. |
| 2011/0242482 | A1* | 10/2011 | Olsen ................ A61B 3/0025 351/205 |
| 2011/0299034 | A1 | 12/2011 | Walsh et al. |
| 2012/0069298 | A1 | 3/2012 | Ng |
| 2012/0095370 | A1 | 4/2012 | Wanders et al. |
| 2012/0150029 | A1 | 6/2012 | Debuc |
| 2012/0162607 | A1 | 6/2012 | Norrby |
| 2012/0188506 | A1 | 7/2012 | Zhou et al. |
| 2012/0271288 | A1 | 10/2012 | Marziliano et al. |
| 2012/0310342 | A1 | 12/2012 | Nguyen et al. |
| 2013/0018276 | A1* | 1/2013 | Zaldivar ............ A61B 3/14 600/558 |
| 2013/0188140 | A1 | 7/2013 | Bagherinia et al. |
| 2013/0235343 | A1 | 9/2013 | Hee et al. |
| 2013/0265542 | A1 | 10/2013 | Frey et al. |
| 2013/0282116 | A1* | 10/2013 | Van Der Mooren .................. A61B 3/1005 623/6.22 |
| 2014/0316389 | A1 | 10/2014 | Schuele et al. |

FOREIGN PATENT DOCUMENTS

| | | |
|---|---|---|
| WO | 2008148517 A1 | 12/2008 |
| WO | 2010147455 A1 | 12/2010 |

OTHER PUBLICATIONS

Athanassius Tadros, Maged Habib, Deepak Tejwani, Hirut Von Lany, Peter Thomas. Opposite clear corneal incisions on the steep meridian in phacoemulsification: Early effects on the cornea. J Cataract Refract Surg 2004; 30:414-417.
Carl Zeiss Meditec AG, "Determination of Central Anterior Chamber Depth with Zeiss SL 120 and SL 130 Slit Lamps", (http://www.meditec.zeiss.com/88256DE3007B916B/0/2E97F19101D02133C1257B18004D25E9/$file/determination_of_central_anterior_chamber_depth_with_zeiss_sl_120_and_sl_130_slit_lamps_sec.pdf).
Donald Sanders, John Retzlaff, Manus Kraff, Richard Kratz, James Gills, Robert Levine, Michael Colvard, John Weisel, Thomas Loyd. Comparison of the accuracy of the Binkhorst, Colenbrander, and SRK™ implant power prediction formulas. Am Intra-Ocular Implant Soc J—vol. 7, Fall 1981.
Douthwaite, W. A. et al., "Slit-lamp measurement of the anterior chamber depth", British Journal of Ophthalmology, 1986, 70, pp. 205-208.
Evdoxia Terzi, Li Wang, Thomas Kohnen. Accuracy of modern intraocular lens power calculation formulas in refractive lens exchange for high myopia and high hyperopia. J Cataract Refract Surg 2009; 35:1181-1189.
Extended European Search Report issued in corresponding European application No. EP 14 00 1507, date of completion of the search Sep. 19, 2014.
Final Office Action, dated Jul. 30, 2015, from corresponding U.S. Appl. No. 13/871,301.
Hirnschall, N. et al., "Predicting the Post-Operative Intraocular Lens Position using Optical Coherence Tomography During Cataract Surgery," 2012 ARVO Annual Meeting.
John Retzlaf. A new intraocular lens calculation formula. Am Intra-Ocular Implant Soc J—vol. 6, Apr. 1980.
John Retzlaff. Posterior chamber implant power calculation: regression formulas. Am Intra-Ocular Implant Soc J—vol. 6. Jul. 1980.
Julio Narva'ez, Grenith Zimmerman, R. Doyle Stulting, Daniel H. Chang. Accuracy of intraocular lens power prediction using the Hoffer Q, Holladay 1, Holladay 2, and SRK/T formulas. J Cataract Refract Surg 2006; 32:2050-2053.
Kenneth J. Hoffer. Clinical results using the Holladay 2 intraocular lens power formula. J Cataract Refract Surg 2000; 26:1233-1237.
Maya Eibschitz-Tsimhoni, Steven M. Archer, and Monte A. Del Monte. Intraocular Lens Power Calculation in Children. Surv Ophthalmol 52:474-482, 2007.
Meeting Abstract, Himschall, Nino et al., "Predicting the Post-operative Intraocular Lens Position Using Optical Coherence Tomography During Cataract Surgery," Investigative Ophthalmology & Visual Science, Mar. 2012, vol. 53, 6718.
N. Himschall et al., "Intra-OP OCT for enhancing IOL power calculation", VIROS (Vienna Institute for Research in Ocular Surgery), First Intra-Operative OCT Science Day, 2014, pp. 1-18.
N. Himschall et al., "Predicting the Postoperative Intraocular Lens Position Using Continuous Intraoperative Optical Coherence Tomography Measurements", Investigative Ophthalmology & Visual Science, vol. 54, No. 8, Aug. 2013, pp. 5196-5203.
N. Himschall et al., "Using continuous intraoperative optical coherence tomography measurements of the aphakic eye for intraocular lens power calculation", British Journal of Ophthalmology, 2014, pp. 1-4.
N. Himschall, S. Amir-Asgari, S. Maedel, O. Findl. Predicting the Postoperative Intraocular Lens Position Using Continuous Intraoperative Optical Coherence Tomography Measurements. Presented at the annual meeting of the Association for Research in Vision and Ophthalmology, Fort Lauderdale, Florida, May 2012.

(56) References Cited

OTHER PUBLICATIONS

N.E. Sverker Norrby, Gabor Koranyi. Prediction of intraocular lens power using the lens haptic plane concept. J Cataract Refract Surg—vol. 23, Mar. 1997.
Office Action, dated Mar. 20, 2017, from corresponding U.S. Appl. No. 13/871,301.
Office Action, dated Nov. 19, 2014, from corresponding U.S. Appl. No. 13/871,301.
Paul-Rolf Preussner, Jochen Wahl, Daniela Weitzel, Silke Berthold, Katharina Kriechbaum, Oliver Findl. Predicting postoperative intraocular lens position and refraction. J Cataract Refract Surg 2004; 30:2077-2083.
Petros Aristodemou, Nathaniel E. Knox Cartwright, John M. Sparrow, Robert L. Johnston. Formula choice: Hoffer Q, Holladay 1, or SRK/T and refractive outcomes in 8108 eyes after cataract surgery with biometry by partial coherence interferometry. J Cataract Refract Surg 2011; 37:63-71.
Samuel Masket, Seth Everett Masket. Simple regression formula for intraocular lens power adjustment in eyes requiring cataract surgery after excimer laser photoablation. J Cataract Refract Surg—vol. 32, Mar. 2006.
Stifter, Eva et al., "Anterior chamber depth and change in axial intraocular lens position after cataract surgery with primary posterior capsulorhexis and posterior optic buttonholing," Journal Cataract and Refractive Surgery, Fairfax, VA, USA, vol. 34, No. 5, May 1, 2008, pp. 749-754, XP022651179; ISSN: 0886-3350, DOI: 10.1016/J.JCRS.2007.12.035.
Sverker Norrby, Eva Lydahl, Gabor Koranyi, Mikaela Taube. Clinical application of the lens haptic plane concept with transformed axial lengths. J Cataract Refract Surg 2005; 31:1338-1344.
Thomas Olsen, Kirsten Thim, Leif Corydon. Accuracy of the newer generation intraocular lens power calculation formulas in long and short eyes. J Cataract Refract Surg—vol. 17, Mar. 1991 187.
Thomas Olsen, Leif Corydon, Howard Gimbel. Intraocular lens power calculation with an improved anterior chamber depth prediction algorithm. J Cataract Refract Surg—vol. 21, May 1995.
Thomas Olsen. Calculation of intraocular lens power: a review. Acta Ophthalmol. Scand. 2007: 85: 472-485.
Thomas Olsen. Prediction of intraocular lens position after cataract extraction. J Cataract Refract Surg—vol. 12, Jul. 1986.
Thomas Olsen. Prediction of the effective postoperative (intraocular lens) anterior chamber depth. J Cataract Refract Surg—vol. 32, Mar. 2006.

* cited by examiner

METHOD, OPHTHALMIC MEASURING SYSTEMS AND COMPUTER-READABLE STORAGE MEDIUM FOR SELECTING AN INTRAOCULAR LENS

FIELD

The present disclosure relates generally to systems and methods for performing ophthalmic measurements. In particular, some embodiments can be used for determining parameters for selecting an intraocular lens for an eye.

BACKGROUND

In cataract surgeries, surgeons remove the natural lens, which has developed an opacification, from a patient's eye. Typically, the reasons for the opacification are metabolic changes of the fibers of the natural lens over time, which lead to loss of transparency of the natural lens and loss of vision. The natural lens is replaced by an artificial intraocular lens implant.

Monofocal, multifocal and accommodating intraocular lenses of different optical powers are available and the surgeon has to select an intraocular lens, which ensures the best visual performance for the patient.

However, commonly used evaluation methods for determining the appropriate intraocular lens have proven not to be reliable enough when applied to patients covering a wide range of anatomical variances. For some of the patients, this leads to unwanted errors in refractive power of the eye following surgery.

Hence, there exists a need for an improved method for determining an intraocular lens to be inserted into the eye.

SUMMARY

Embodiments provide a method of determining at least one selection parameter for selecting an intraocular lens to be inserted into an eye. The method comprises reading, by a data processing system, data indicative of an axial position of at least a portion of an anterior surface of an at least partially empty capsular bag of the eye, relative to an optical axis of the eye. The method further comprises determining an axial position parameter, which is representative of the axial position of the portion of the anterior surface, depending on the data. The method further comprises determining the at least one selection parameter for selecting the intraocular lens depending on the determined position parameter.

It has been found that based on the axial position parameter of the anterior surface of the at least partially empty capsular bag, it is possible to more reliably determine an intraocular lens, which ensures the best visual performance for the patient. Thereby, the risk for postoperative refractive errors is significantly reduced.

The intraocular lens may be one of a monofocal intraocular lens, a multifocal intraocular lens or an accommodating intraocular lens. The intraocular lens may be toric or non-toric. A refractive surface of the intraocular lens may be rotationally symmetric and/or aspherical. A refractive surface of the intraocular lens may be a free-form surface.

The at least partially empty capsular bag may be formed by removing at least a portion of the natural lens from the capsular bag. This may include one or a combination of the following procedures: phakoemulsification, extracapsular cataract extraction (ECCE) and intracapsular cataract extraction (ICCE). An eye, which has all of the natural lens removed, i.e. an eye with an empty capsular bag, may be referred to as an aphakic eye.

The data processing system may be a computer system. The data processing system may include one or a combination of a system housing, input and/or output units, a storage system, which may comprise volatile and/or non-volatile memory, processors such as microprocessors and/or digital signal processors, operating systems, drivers, graphical user interfaces, application programs, and an interface for reading the data from an ophthalmic measurement device.

The optical axis of the eye may be defined as an axis connecting the centers of curvatures of the refracting surfaces of the eye. The optical axis may refer to the refracting surfaces of the eye before the natural lens has been at least partially removed. In other words, the optical axis may refer to a phakic eye.

The axial position of the anterior surface portion is an axial position relative to the optical axis of the eye. The axial position may be measured relative to an axial position of a reference structure of the eye. The reference structure may be for example a central portion of the cornea, an apex of the cornea or the retina. The reference structure may be located outside the capsular bag. A position of the reference structure may be unaffected by the removal of the natural lens and/or by the insertion of the intraocular lens.

The data may have been acquired after the natural lens has been at least partially removed from the capsular bag.

According to an embodiment, the data have been acquired with or without an intraocular lens being contained in the capsular bag. Additionally or alternatively, the data may have been acquired with or without a capsular tension ring being contained in the capsular bag.

The anterior surface may be located at a radial distance from the optical axis of the eye. The anterior surface may comprise an opening. The optical axis may pass through the opening. The opening may have been formed in the anterior surface to remove at least a portion of the natural lens from the capsular bag. The opening may have been formed by capsulorhexis and/or by anterior capsulotomy. Additionally or alternatively, the opening may serve to implant the intraocular lens into the capsular bag.

One of the at least one selection parameters may be an optical power of the intraocular lens. The optical power may be an optical power of a monofocal intraocular lens or an optical power of a range of optical powers provided by a multifocal intraocular lens or an accommodating intraocular lens.

Determining the optical power may comprise determining an effective lens position and/or a predicted postoperative anterior chamber depth depending on the axial position parameter of the anterior surface portion. The optical power may be determined depending on the effective lens position and/or the predicted postoperative anterior chamber depth.

The optical power may be determined depending on the effective lens position and/or the predicted postoperative anterior chamber depth by geometrical optics. The cornea and/or the intraocular lens may be described by a thin lens approximation or a thick lens approximation.

Additionally or alternatively, one of the at least one selection parameter may be a predicted postoperative anterior chamber depth. The predicted postoperative anterior chamber depth may be defined as a prediction of the distance between the outer surface of the corneal apex and the anterior apex of the intraocular lens after the intraocular lens has been inserted into the eye.

Additionally or alternatively, one of the at least one selection parameters may be an effective lens position of the intraocular lens. The effective lens position may be defined as a location of a principal plane of the intraocular lens relative to the outer surface of the corneal apex. The effective lens position may be defined by assuming thin-lens behavior or thick-lens behavior of the cornea and/or the intraocular lens.

Additionally or alternatively, one of the at least one selection parameters may be a range of optical powers provided by a multifocal intraocular lens or provided by an accommodating intraocular lens.

Additionally or alternatively, one of the at least one selection parameters may be a geometrical parameter of the optical element of the intraocular lens and/or a geometrical parameter of a haptics of the intraocular lens. The geometrical parameter of the optical element may be a diameter of the optical element.

According to a further embodiment, the method comprises inserting the intraocular lens into the eye. The intraocular lens may be inserted into the capsular bag. Alternatively, the intraocular lens may be fixated to other structures of the eye, such as the iris or the anterior chamber angle.

According to a further embodiment, the method comprises acquiring the data by irradiating the eye with electromagnetic radiation and/or ultrasound radiation. The electromagnetic radiation and/or ultrasound radiation may be emitted by an ophthalmic measuring system.

The electromagnetic radiation may have a wavelength of between 300 nanometers and 2000 nanometers. The electromagnetic radiation may be a beam of a laser and/or a light beam of an optical coherence tomography (OCT) system. The ophthalmic measuring system may be configured to scan a portion of the eye with a beam of the electromagnetic radiation. The ultrasound radiation may be generated by an ultrasound microscope. The data may further be generated by detecting a portion of the electromagnetic radiation and/or ultrasound radiation, which has been scattered at structures of the eye.

According to a further embodiment, the ophthalmic measuring system comprises an optical coherence tomography (OCT) system, a slit lamp, a Scheimpflug imaging system, an ultrasound microscope, a laser scanning microscope and/or an optical imaging microscope, wherein the optical imaging microscope is configured to image an object plane onto an image plane.

The slit lamp may be configured to perform measurements according to the Smith method. A portion of the eye may be arranged in the object plane of the optical imaging microscope. The OCT system may be a time domain OCT system (TD-OCT) and/or a frequency domain OCT system (FD-OCT). The frequency domain OCT system may be a spatially encoded frequency domain OCT system (also denoted as spectral domain OCT or Fourier domain OCT) and/or a time encoded frequency domain OCT system (also denoted as swept source OCT).

Embodiments provide a method of determining at least one selection parameter for selecting an intraocular lens to be inserted into an eye. The method comprises acquiring, by an OCT system, OCT data of at least a portion of an at least partially empty capsular bag of the eye. The method further comprises determining at least one of a position parameter and a geometrical parameter of the portion of the capsular bag, depending on the OCT data. The method further comprises determining the at least one selection parameter depending on the at least one of the position parameter and the geometrical parameter.

The position parameter may be measured relative to a reference structure of the eye.

The geometrical parameter may be a parameter, which at least partially describes a geometry of the portion of the capsular bag. The geometrical parameter may be a radius of curvature, a thickness, a length, or a diameter of the portion of the capsular bag. The geometrical parameter may be an inner equatorial diameter of the capsular bag.

According to an embodiment, the position parameter is representative of an axial position relative to the optical axis of the eye. The axial position parameter may be representative of an axial position of a portion of the anterior surface of the capsular bag.

Alternatively, the position parameter may be representative of an axial position of at least a portion of the posterior surface of the capsular bag relative to the optical axis of the eye. Alternatively, the position parameter may be representative of an axial position of an equator of the capsular bag and/or may be a parameter of an orientation of the equator relative to the optical axis of the eye.

The OCT-data may have been acquired after the natural lens has been at least partially removed from the capsular bag and before the intraocular lens has been implanted into the eye. Alternatively, the capsular bag may contain the intraocular lens when the OCT data are acquired. The OCT data may be acquired with or without a capsular tension ring being contained in the capsular bag.

According to an embodiment, at least a portion of the data, which is indicative of the axial position of the anterior surface portion, represents a two-dimensional cross section. According to an embodiment, the OCT data of the portion of the at least partially empty capsular bag represents a two-dimensional cross-section. The two-dimensional cross-section may be an image.

The cross-section may be oriented such that it includes or substantially includes the optical axis of the eye. An angle between a plane of the cross-section and the optical axis may be less than 20 degrees, or less than 10 degrees, or less than 5 degrees.

According to an embodiment, the determining of the axial position parameter comprises measuring an axial distance along the optical axis of the eye between an axial position of the anterior surface portion and an axial position of a central portion of the cornea. The central portion may be an apex of the cornea.

The axial distance may be measured between an axial position of an inner or outer surface of the central portion of the cornea and the axial position of the anterior surface portion.

According to an embodiment, the determining of the axial position parameter comprises determining an axial position of a portion of an edge of an opening in the anterior surface relative to the optical axis of the eye.

The method may comprise determining a connecting line between two substantially opposing portions of the edge. The connecting line may be oriented substantially perpendicular to the optical axis of the eye. The method may comprise determining a distance line between the connecting line and a central portion of the apex. The distance line may be determined such that the distance line and the connecting line intersect at right angles. The distance line may be determined such that it is substantially oriented along the optical axis of the eye. The method may comprise determining a minimum distance between the central portion of the cornea and the connecting line.

According to an embodiment, the determining of the one or more selection parameters comprises performing a regression analysis. At least one input variable of the regression analysis may be determined depending on the position parameter and/or geometrical parameter of the portion of the capsular bag. In particular, the input variable may be determined depending on the axial position parameter of the anterior surface portion of the capsular bag.

The regression analysis may be configured to establish a relationship between one or more input variables and one or more output variables. The output variables may be one or more selection parameters. The regression analysis may be a linear or a non-linear regression analysis.

The input variables of the regression analysis may comprise one or a combination of the refractive power of the cornea, one or more radii of curvature of the cornea, the axial length of the eye, the central cornea thickness, the position parameter and/or geometrical parameter of the portion of the capsular bag, and the axial position parameter of the anterior surface portion. The one or more radii of curvature of the cornea may be measured at the apex of the cornea.

The refractive power of the cornea, the axial length of the eye, the one or more radii of curvature of the cornea may have been measured before the natural lens has been at least partially removed from the capsular bag. In other words, these parameters may be preoperative parameters. The central cornea thickness may be measured before or after the natural lens has been at least partially removed from the capsular bag.

According to a further embodiment, the regression analysis comprises a partial least squares regression analysis. The partial least squares regression analysis may be a linear or a non-linear partial least squares analysis.

According to an embodiment, the determining of the selection parameter comprises calculating an image formation performed by a cornea of the eye and the intraocular lens depending on the position parameter and/or the geometrical parameter of the portion of the capsular bag, in particular depending on the axial position parameter of the anterior surface portion.

Thereby, an alternative or additional method to regression analysis is provided for selecting the intraocular lens. The image formation calculation may comprise calculating parameters of the imaging of an object plane onto an image plane. The image formation calculation may be based on an assumed imaging behavior of the cornea and/or the intraocular lens, such as a thin-lens behavior or a thick-lens behavior. The image formation calculation may comprise defining one or more principal planes for the cornea and/or the intraocular lens. The image formation calculation may comprise performing ray tracing. Further details for a method of selecting an intraocular lens by using a simulation based on an eye model can be found in German patent application DE 10 2013 002 293. The content of this document is incorporated herein by reference in its entirety.

According to a further embodiment, the method comprises removing at least a portion of the natural lens from the capsular bag to form the at least partially empty capsular bag.

According to a further embodiment, the method comprises selecting the intraocular lens from a stock of different intraocular lenses depending on the determined one or more selection parameters.

According to a further embodiment, the method comprises implanting a capsular tension ring into the capsular bag.

The capsular tension ring may be configured to apply an outward pressure at an equatorial region of the capsular bag.

The data may be acquired when the capsular tension ring is in the capsular bag. The capsular tension ring may be configured to keep central portions of the anterior and/or posterior surfaces of the capsular bag in a substantially flat shape.

According to a further embodiment, the method comprises reading data indicative of a refractive power of the cornea. The determining of the selection parameter may be performed depending on the refractive power of the cornea. The refractive power may be a local mean surface refractive power of the cornea.

According to a further embodiment, the method comprises reading data indicative of an axial length of the eye. The determining of the selection parameter may be performed depending on the axial length. The axial length may be measured by using electromagnetic radiation and/or ultrasound radiation, e.g. by using an ultrasound microscope and/or an OCT system.

According to a further embodiment, the determining of the selection parameter is further performed depending on at least one anatomical parameter of the eye, which has been acquired before the at least partially empty capsular bag has been formed by removing at least a portion of a natural lens of the eye. In other words, the determining of the selection parameter is performed depending on preoperative parameters.

According to a further embodiment, the method comprises acquiring intraocular pressure data indicative of an intraocular pressure of the eye.

The intraocular pressure data may be acquired by tonometry. The method may further comprise controlling the intraocular pressure during the acquiring of the data for determining the position parameter and/or geometrical parameter of the portion of the capsular bag and/or the axial position parameter of the anterior surface portion.

Embodiments provide a computer program product comprising a computer useable medium having computer program logic recorded thereon for enabling a processor to perform the method of any one of the preceding embodiments. The computer useable medium may be a non-transitory storage medium.

Embodiments provide a system for determining at least one selection parameter for selecting an intraocular lens to be inserted into an eye. The system comprises a data processing system, configured to read data indicative of an axial position of at least a portion of an anterior surface of a an at least partially empty capsular bag of the eye, relative to an optical axis of the eye. The system further comprises a processing unit, configured to determine an axial position parameter, which is representative of the axial position of the portion of the anterior surface, depending on the data. The processing unit is further configured to determine the at least one selection parameter for selecting an intraocular lens depending on the determined position parameter.

Embodiments provide a system for determining at least one selection parameter for selecting an intraocular lens to be inserted into an eye. The system comprises an OCT system configured to acquire OCT data of at least a portion of an at least partially empty capsular bag of the eye. The system further comprises a data processing system configured to determine at least one of a position parameter and a geometrical parameter of the portion of the capsular bag, depending on the OCT data. The data processing system is further configured to determine the at least one selection parameter for selecting the intraocular lens, depending on the at least one of the position parameter and the geometrical parameter.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1A:
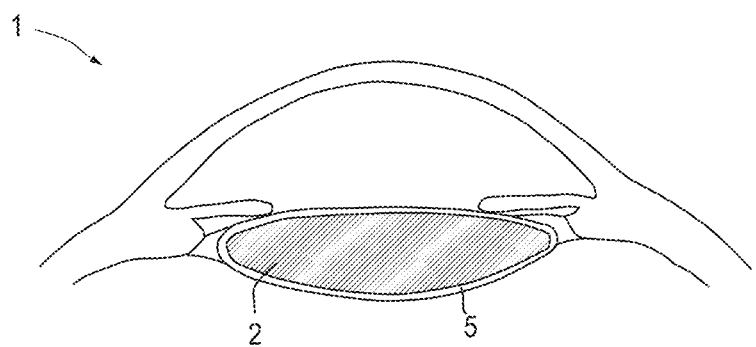
FIGS. 1A, 1B and 1C are schematic illustrations of main stages of cataract surgery.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 1B:
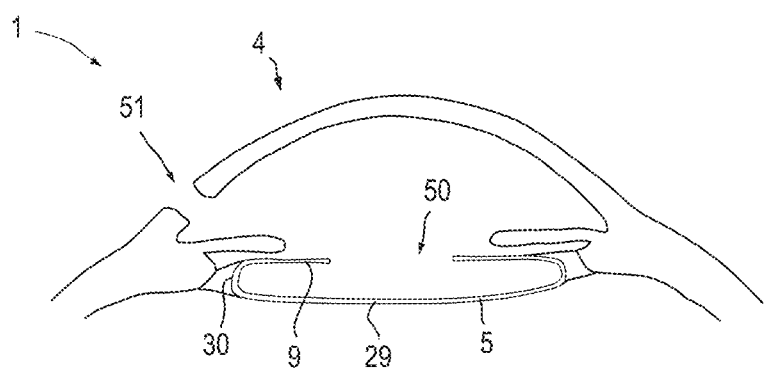
Figure 1C:
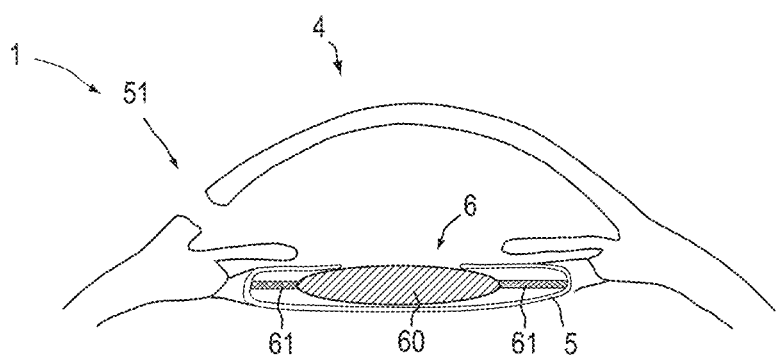

FIGS. 1A, 1B and 1C schematically illustrate major stages of cataract surgery.

FIG. 1A shows an eye 1 with cataract. Cataract is a clouding of the natural lens 2 inside the capsular bag 5 of the eye 1, which leads to a decrease in vision. Visual loss occurs because the opacification of the natural lens 2 obstructs light from passing and being focused onto the retina at the back of the eye 1.

Generally, in cataract surgery, the natural lens 2 is replaced by an artificial intraocular lens. The surgeon usually forms an opening 50, as shown in FIG. 1B, in an anterior surface 9 of the capsular bag 5 and removes the natural lens 2 e.g. by using a phakoemulsificator. FIG. 1B shows the eye 1 after this process, with the natural lens 2 removed from within the capsular bag 5. An incision 51 is formed in the cornea 4, for inserting surgical instruments into the anterior chamber of the eye.

The capsular bag 5 comprises an anterior surface 9 and a posterior surface 29. An equator 30 of the capsular bag 5 separates the anterior surface 9 from the posterior surface 29.

FIG. 1C shows the eye 1 in a state after an intraocular lens 6, has been implanted. The intraocular lens 6 is typically implanted within the capsular bag. The intraocular lens 6 usually consists of a plastic lens 60 with plastic side struts 61, called haptics to hold the intraocular lens 6 in place within the capsular bag 5.

Intraocular lenses are available as monofocal lenses, toric lenses, multifocal lenses, and accommodating lenses. The appropriate optical power of the intraocular lens has to be determined prior to its insertion into the eye. Accurate calculation of the power of the intraocular lens is an important factor to minimize errors in refractive power of the eye following surgery.

Figure 2:
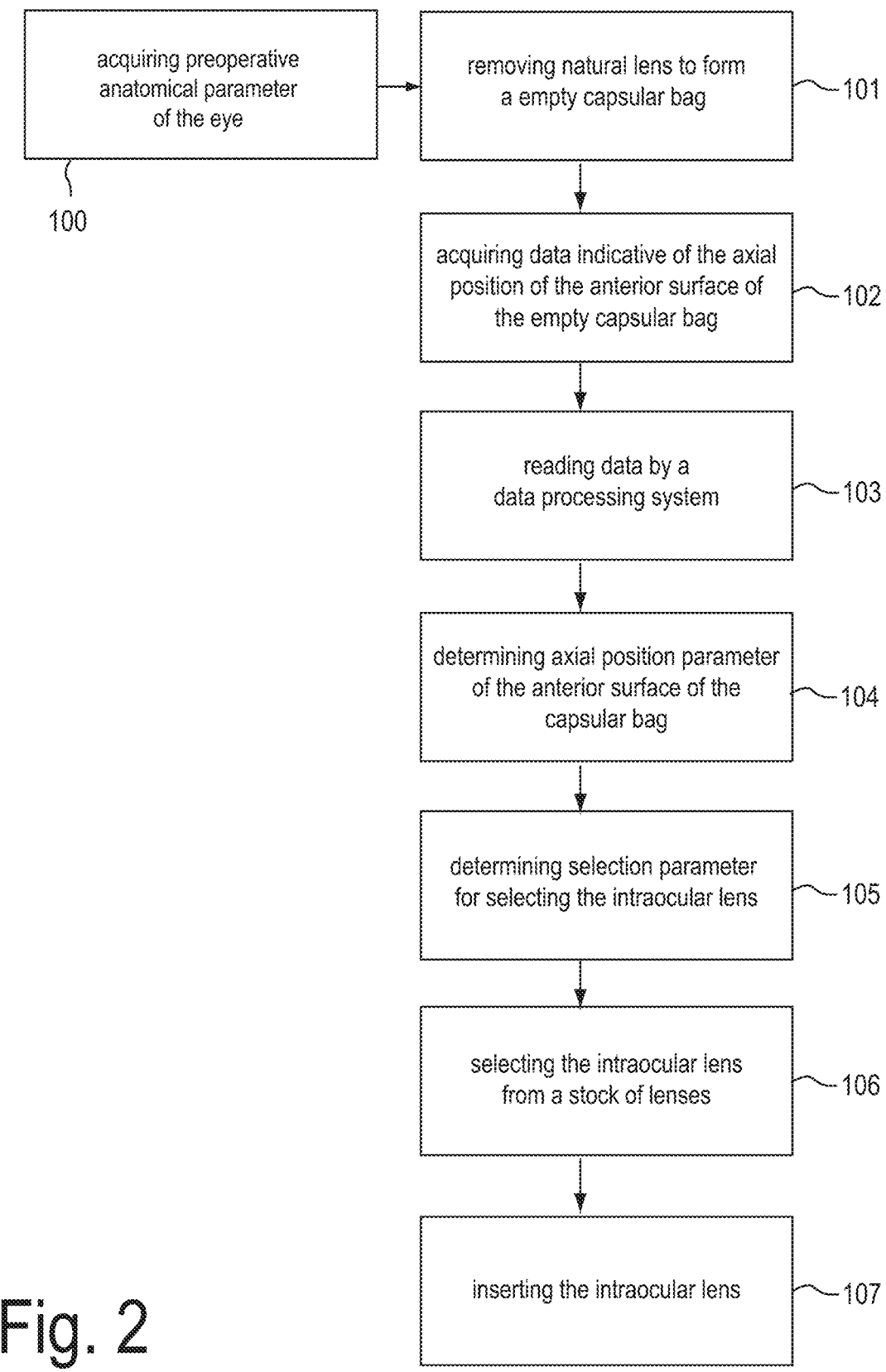
FIG. 2 is a flow chart illustrating an exemplary method for determining a selection parameter for selecting an intraocular lens.

FIG. 2 illustrates an exemplary method for selecting the intraocular lens in a cataract surgery.

Before the natural lens is removed from the eye, preoperative anatomical parameters of the eye are acquired 100. The preoperative anatomical parameters may comprise one or a combination of the refractive power of the cornea, the axial length of the eye, one or more radii of curvature of the cornea and the central cornea thickness.

Then, the natural lens is removed 101 from the capsular bag of the eye. This may be performed by one or a combination of the following procedures (i) phakoemulsification, (ii) manual small incision cataract surgery (MSICS), (iii) extracapsular cataract extraction (ECCE). After removal of the intraocular lens, an empty capsular bag is left in the eye, into which the intraocular lens will later be inserted.

In order to determine the optical power of the intraocular lens, an ophthalmic measuring system is used to acquire 102 data, which are indicative of the axial position of a portion of the anterior surface of the empty capsular bag relative to the optical axis of the eye. The ophthalmic measuring system may for example be an OCT system. The data represent a two-dimensional cross-sectional image of a portion of the anterior segment of the eye.

During the acquiring 101 of the data, the intraocular pressure of the eye may be controlled. Controlling the intraocular pressure may comprise adjusting the intraocular pressure to a predefined value. The predefined value may be for example 2666 Pa, which corresponds to 20 mm Hg. Adjusting the intraocular pressure may be performed by adjusting a height difference between an infusion container and the eye. The infusion container may contain an irrigation fluid. The infusion container may be connected to the eye by a flexible tubing to provide a controlled flow of the irrigation fluid into the anterior chamber of the eye.

Then, the data are read 103 by a data processing system and stored in a storage system of the data processing system. The data processing system comprises a processing unit, which is configured to determine 104 a position parameter and/or a geometrical parameter of a portion of the empty capsular bag measured along the optical axis of the eye and measured relative to a further anatomical structure of the eye, such as the cornea. The position parameter may be an axial position parameter measured as a distance between the axial position of a portion of the anterior surface of the capsular bag and the axial position of the apex of the cornea.

After the position parameter and/or the geometrical parameter has been calculated, the processing unit determines 105 a selection parameter for selecting the appropriate intraocular lens depending on the position parameter and/or the geometrical parameter. The selection parameter may be for example the optical power of the intraocular lens or the predicted postoperative anterior chamber depth.

Depending on the determined selection parameter, the intraocular lens is selected 106 from a stock of intraocular lenses and inserted 107 into the emptied capsular bag of the eye.

Figure 3:
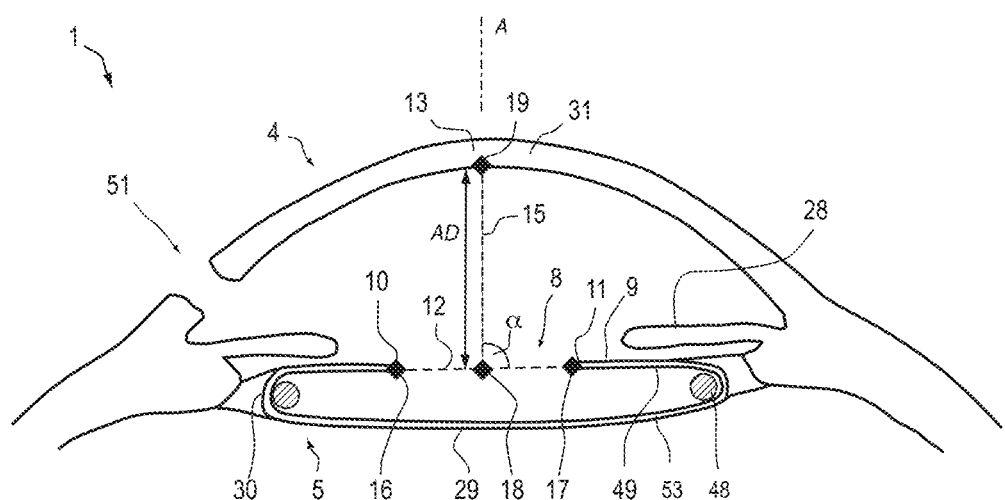
FIG. 3 is a schematic illustration of how the axial position of the anterior surface of the capsular bag is determined in the exemplary method, illustrated in FIG. 2.

With reference to FIG. 3, an exemplary process of determining the axial position parameter of a portion of the anterior surface 9 of the capsular bag 5, is described. FIG. 3 schematically illustrates a cross-sectional image, which is represented by the acquired data. The cross-sectional image may be acquired by an OCT system. The cross-sectional image shows the anterior segment of the eye 1 in a state after the natural lens 2 (shown in FIG. 1A) has been removed from the capsular bag 5.

The image shows edge portions 10, 11 of the opening 8 in the anterior surface 9 of the capsular bag 5. The natural lens has been removed through the opening 8. The image further shows the incision 51 in the cornea 4, through which surgical instruments have been inserted for forming the opening 8 and for removing the natural lens.

After removal of the natural lens and before acquiring the image data, a capsular tension ring 48 has been inserted into the capsular bag 5. Although the cross-section of the capsular tension ring 48 is fully depicted in FIG. 3, the cross-section of the capsular tension ring 48 may be only partially visible in the OCT image. The capsular tension ring 48 keeps portions of the anterior surface 9 of the capsular bag 5 and portions of the posterior surface 29 of the capsular bag 5 in a substantially flat shape.

It has been shown that by acquiring data of a portion of the capsular bag 5 with the capsular tension ring 48 being contained in the capsular bag 5, the position parameter and/or geometrical parameter can be determined with higher accuracy. This leads to less postoperative refractive errors of the selected intraocular lens.

However it has also been shown that sufficiently low postoperative refractive errors can be obtained by determining position parameters and/or geometrical parameters without the capsular tension ring 48 being contained in the capsular bag 5.

It has further been shown that by using OCT, it is possible to acquire image data of outer portions 49 of the anterior surface 9 and outer portions 53 of the posterior surface 29, which are located beneath the iris 28. Thereby, position parameters and/or geometrical parameters of the capsular bag 5 can be more reliably determined.

The acquired data are read by a data processing system and displayed on a display device of the data processing system. A first line 12 is determined, which connects opposing portions 10, 11 of the edge of the opening 8. Also, a second line 15 is determined, which connects an apex 13 of the cornea 4 with the first line 12 such that the first and the second line 12, 15 intersect at an angle a of 90 degrees. Since the opposing portions 10, 11 of the edge are approximately located in a plane, which is oriented perpendicular to the optical axis, the second line 15 is oriented along the optical axis A of the eye 1 with a sufficiently high accuracy. The optical axis A passes through the apex 13 of the cornea 4.

The data processing system may be configured to determine the first and the second line 12, 15 by applying an image processing algorithm to the image. The image processing algorithm may perform segmentation of the image. The segmentation may comprise one or a combination of the following methods: a pixel-oriented method, an edge-oriented method, a region-oriented method, a model-based method, a texture-based method and/or a color-oriented method. In particular, the segmentation may comprise a model-based segmentation method depending on a model of the anterior segment of the eye.

Additionally or alternatively, the data processing system may be configured to display the image on a display, thereby allowing the user to identify in the displayed image a starting point 16, an endpoint 17 of the first line 12, and the apex 13 of the cornea 4. In response to the user input, the data processing system then may calculate the intersection point 18 such that the first and the second line 12, 15 intersect at an angle a of 90 degrees.

After the first and the second lines 12, 15 have been determined, the data processing system determines an intersection point 19 of an inner surface of the cornea 4 with the second line 15. Additionally or alternatively, the user may determine the intersection point 19 of the inner surface with the second line 15.

Then, the data processing system calculates a distance between the intersection point 19 and the intersection point 18, where the first line 12 intersects the second line 15. Hence, the distance is measured along a distance line, which connects the central portion of the cornea with the first line 12. The distance line is oriented along the second 15 line and along the optical axis of the eye. The determined distance represents the axial distance AD between a portion of the anterior surface 9 of the capsular bag 5 and the apex 13 of the cornea 4 and, hence, the axial position of the anterior surface portion of the empty capsular bag 5.

The distance AD is used to calculate a selection parameter, for selecting the intraocular lens. The selection parameter may be for example the optical power of the intraocular lens, the predicted postoperative anterior chamber depth, or the effective lens position.

The predicted postoperative anterior chamber depth may be defined as the distance between the outer surface of the corneal apex and the anterior apex of the intraocular lens, after the intraocular lens has been inserted into the eye. The postoperative anterior chamber depth can be measured, e.g. by using an ultrasound microscope or an OCT system, after the intraocular lens has been implanted.

The effective lens position may be defined as the location of a principal plane of the intraocular lens relative to the outer surface of the corneal apex. The effective lens position may be closely related to the predicted postoperative anterior chamber depth, the difference being independent from the anatomy of the eye.

In the exemplary method, the selection parameter is the predicted postoperative anterior chamber depth. The predicted postoperative anterior chamber depth is determined depending on the determined axial position of the anterior surface portion of the empty capsular bag.

More specifically, the predicted postoperative anterior chamber depth $ACD_{postOP}$ is determined according to the following equation:

$$ACD_{postOP} = a_0 + a_1 \cdot (AD + CCT) + a_2 \cdot AL_{pre}, \quad (1)$$

wherein AD denotes the axial position of the anterior surface portion of the capsular bag, as determined by the axial distance between the axial position of the inner surface of the apex of the cornea and the axial position of the portion of the anterior surface of the capsular bag. CCT denotes the central cornea thickness, i.e. the distance between the inner surface of the corneal apex and the outer surface of the corneal apex. $AL_{pre}$ denotes the preoperative axial length of the eye, i.e. the axial length measured before the natural lens is removed.

It is also conceivable that the predicted postoperative anterior chamber depth is calculated according to equation (1), however without the central cornea thickness CCT being an input variable. In this alternative equation, which is based on equation (1), the constant $a_1$ is multiplied only with the axial position of the anterior surface portion AD.

The constants $a_0$, $a_1$ and $a_2$ of equation (1) are determined by a regression analysis from data obtained by evaluating a number of intraocular lens implantation surgeries. In each of the surgeries, the axial length $AL_{pre}$ has been determined before the natural lens has been removed. The central cornea thickness CCT has been measured before the natural lens has been removed. However, it is also possible to measure the central cornea thickness after the natural lens has been removed. The axial position of the anterior surface portion AD has been determined after removal of the natural lens and before implantation of the intraocular lens. The postoperative anterior chamber depth $ACD_{postOP}$ has been determined after the implantation of the intraocular lens.

The implantation surgeries, which are analyzed for determining the constants $a_0$, $a_1$ and $a_2$ may relate to a specific design of the intraocular lens, to a specific surgical technique used for removing the natural lens, to a specific surgical technique used for implanting the IOL, and/or to the surgeon who performed the surgery.

Thereby, the determined constants $a_0$, $a_1$ and $a_2$ may be specifically determined for a specific IOL design, for a specific surgical technique, and/or for a specific surgeon.

It has been shown that by using equation (1) with constants $a_0$, $a_1$ and $a_2$ determined by regression analysis, it is possible to select the intraocular lens such that the risk for postoperative refractive errors is significantly reduced.

The following values for the constants $a_0$, $a_1$ and $a_2$ have been obtained by the linear regression analysis:

$$a_0 = -0.325 \text{ mm}$$

$$a_1 = 0.592$$

$$a_2 = 0.066, \tag{2}$$

with an absolute value of the Pearson correlation coefficient being $|r|=0.73$. The high absolute value of the Pearson correlation coefficient indicates that the postoperative anterior chamber depth can be predicted with high reliability based on the axial position of the anterior surface of the capsular bag. A statistical P value of 0.000 has been obtained for the sum of the axial position of the anterior surface portion AD and the central cornea thickness CCT. A statistical P value of 0.198 has been obtained for the preoperative axial length $AL_{pre}$.

One of the most commonly used formula for calculating the effective lens position is the Haigis formula. The Haigis formula is a linear formula, which is obtained by regression analysis, wherein the preoperative anterior chamber depth and the axial length serve as input variables. Hence, in contrast to formula (1) above, all input variables of the Haigis formula are measured before the natural lens is removed from the capsular bag. The output variable of the Haigis formula is the effective lens position, which is closely related to the predicted postoperative anterior chamber depth, which is the output variable of formula (1) above. Depending on the effective lens position, the optical power of the intraocular lens can be calculated.

In order to compare the reliability of the Haigis formula with the reliability of formula (1), a linear regression analysis has been performed based on the same data of the implantation surgeries and based on the input variables of the Haigis formula:

$$ACD_{postOP} = b_0 + b_1 \cdot ACD_{pre} + b_2 \cdot AL_{pre}, \tag{3}$$

wherein $ACD_{pre}$ denotes the preoperative anterior chamber depth.

The following values for the constants $b_0$, $b_1$ and $b_2$ have been obtained:

$$b_0 = 1.419 \text{ mm}$$

$$b_1 = 0.338$$

$$b_2 = 0.094, \tag{4}$$

with an absolute value of the Pearson correlation coefficient being $|r|=0.49$. A statistical P value of 0.092 has been obtained for the preoperative anterior chamber depth $ACD_{pre}$, and a statistical P value of 0.11 has been obtained for the preoperative axial length $AL_{pre}$.

Since the absolute value of the Pearson correlation coefficient obtained by using equation (1), is significantly greater than the absolute value of the Pearson correlation coefficient obtained by using the input variables of the Haigis formula, the selection of the intraocular lens based on equation (1) is evidently much more reliable.

In what follows, a description is given of an alternative exemplary method of determining a selection parameter. In this exemplary method, the selection parameter is the optical power of the intraocular lens. The optical power is determined by a linear formula, the constants of which are determined by a partial least squares regression (PLSR) analysis. However it is also conceivable that these constants are determined by other techniques of regression analysis.

The input variables of the partial least squares regression analysis are the axial length ($AL_{pre}$), the axial distance of the anterior surface portion of the empty capsular bag (AD), and the local mean surface refractive power of the cornea ($K_{pre}$), which is defined as $$K_{pre} = \frac{0.332}{2} \cdot \left( \frac{1}{r_1} + \frac{1}{r_2} \right), \tag{5}$$

with $r_1$ and $r_2$ being the principal radii of curvature of the cornea. The preoperative local mean surface refractive power is measured at the apex of the cornea.

The axial length and the local mean surface refractive power are determined preoperatively, i.e. before the natural lens is at least partially removed from the capsular bag.

The partial least squares regression analysis is performed for determining the constants $c_0$, $c_1$, $c_2$, and $c_3$ in the following equation:

$$P_{IOL} = c_0 + c_1 \cdot AL_{pre} + c_2 \cdot K_{pre} + c_3 \cdot AD, \tag{6}$$

wherein $P_{IOL}$ is the optical power of the intraocular lens.

The following values have been obtained for the constants $c_0$, $c_1$, $c_2$ and $c_3$:

$$c_0 = 67.5 \text{ diopters}$$

$$c_1 = 4 \text{ diopters/mm}$$

$$c_2 = -36$$

$$c_3 = 2.8 \text{ diopters/mm}. \tag{7}$$

Figure 4:
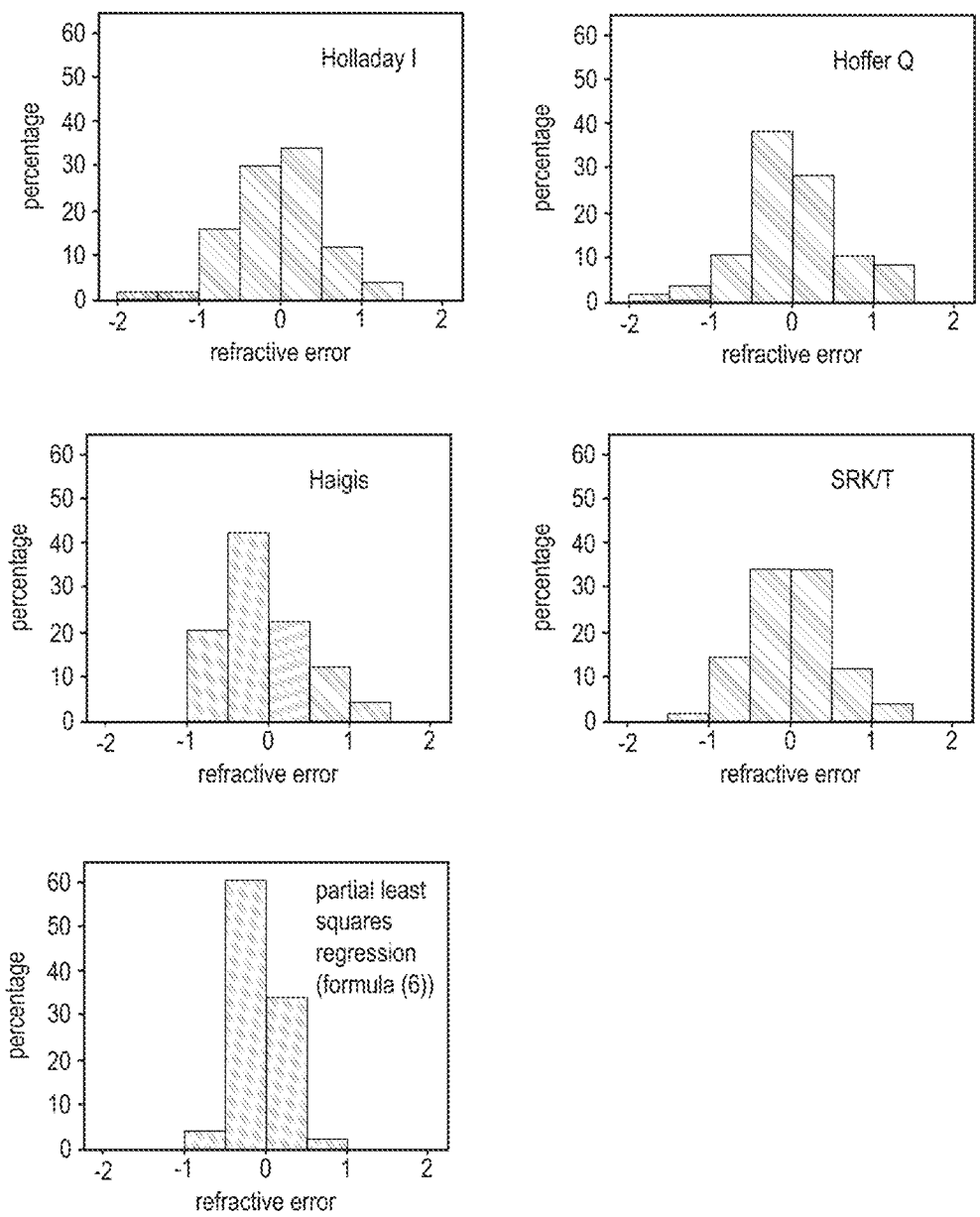
FIG. 4 illustrates postoperative refractive errors obtained with the exemplary method illustrated in FIG. 2, compared to conventional techniques.

FIG. 4 shows postoperative refractive errors occurring when formula (6) is used to determine the optical power of the intraocular lens compared to postoperative refractive errors occurring when conventional techniques for selecting the intraocular lens are applied.

It has been shown that by using the partial least squares analysis with the axial position parameter of the anterior surface of the empty capsular bag as one of the input variables, the optical power of the intraocular lens can be predicted with a high degree of reliability.

The conventional techniques for selecting an intraocular lens evaluated for comparison are the Holladay 1 formula, the Hoffer Q formula, the Haigis formula and the SRK/T formula. None of these conventional methods rely on anatomical parameters, which have been measured with the natural lens removed from the capsular bag.

In each of the bar diagrams of FIG. 4, the x-axis represents the postoperative refraction in diopters and the y-axis represents the corresponding percentage of patients. As can be seen from a comparison of the bar diagrams of FIG. 4, formula (6) allows to calculate the dioptric power of the intraocular lens such that postoperative refractive errors of more than +1 diopters or less than −1 diopters do not occur.

Even more, compared to the results of the conventional formulas, which are shown in FIG. 4, applying formula (6) for selecting the intraocular lens also yields a considerably higher number of patients, which have a postoperative refractive error, which is between −0.5 diopters and +0.5 diopters.

Hence, it can be concluded that postoperative refractive errors can be significantly reduced by using the partial least squares regression analysis with the axial position parameter of the anterior surface of the empty capsular bag as an input variable.

Figure 5:
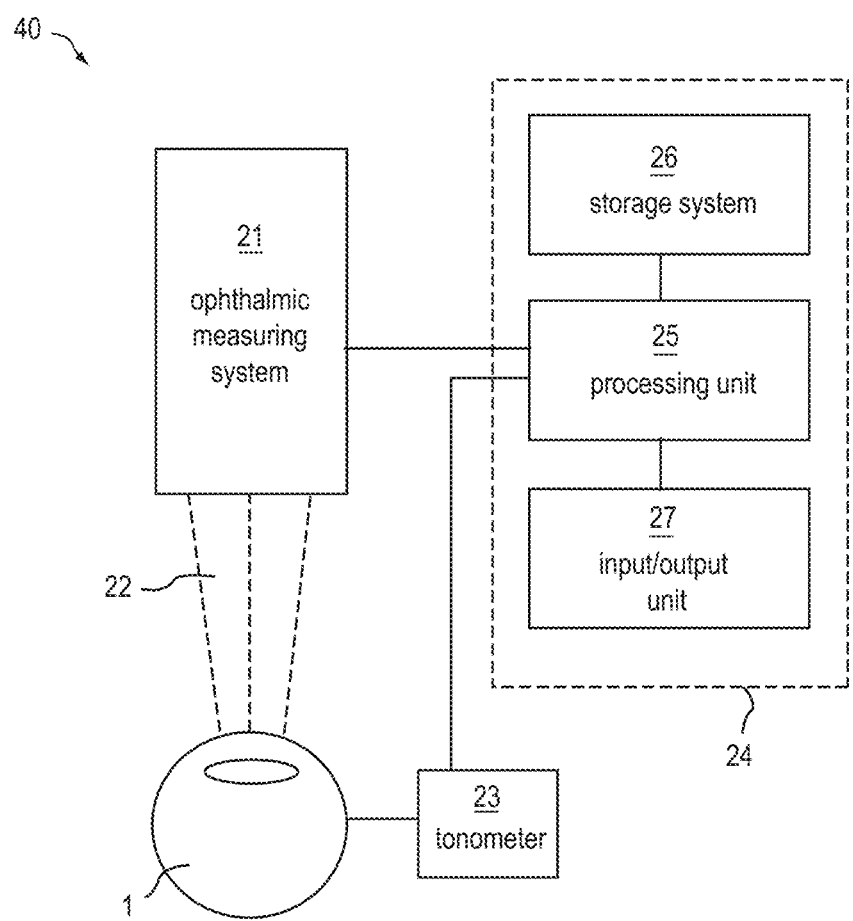
FIG. 5 is a schematic illustration of a system, which is configured to perform the exemplary method, as illustrated in FIG. 2.

FIG. 5 is a schematic illustration of a system 40 for determining the optical power of the intraocular lens according to an exemplary embodiment. The system 40 comprises an ophthalmic measuring system 21. The ophthalmic measuring system 21 is configured to acquire data of a portion of an at least partially empty capsular bag. The data may be indicative of an axial position of at least a portion of the anterior surface of the capsular bag. In other words, the data may be configured such that an axial position of the anterior surface portion may be derivable.

The ophthalmic measuring system 21 is configured to irradiate the eye with electromagnetic radiation and/or ultrasound radiation. The ophthalmic measuring system 21 also comprises a detector system for detecting electromagnetic radiation and/or ultrasound radiation, which has been scattered from structures of the eye.

The ophthalmic measuring system 21 may be one or a combination of an OCT system, a slit lamp, a Scheimpflug imaging system, an ultrasound microscope, a laser scanning microscope and an optical imaging microscope, wherein the optical imaging microscope is configured to form an image of an object plane in an image plane of the optical imaging microscope.

An example of a Scheimpflug imaging system is the Pentacam™ imaging system manufactured by Oculus of Heidelberg, Germany. The Pentacam™ imaging system comprises a rotating Scheimpflug camera which captures Scheimpflug images of the anterior eye segment. The Scheimpflug principle provides images that include information from the anterior corneal surface to the posterior lens capsule.

The slit lamp may be configured to perform measurements, as suggested by Smith. The configuration of such a slit lamp is described by W. A. Douthwaite and D. Spence in the article entitled "Slit-lamp measurement of the anterior chamber depth", published in the British Journal of Ophthalmology (1986), 70, p. 205-208. The content of this document is incorporated herein by reference in its entirety. The method of slit lamp measurements a suggested by smith is further described in the article "Determination of Central Anterior Chamber Depth with Zeiss SL 120 and Zeiss SL 130 Slit Lamps" (available for download from http://www-.meditec.zeiss.com/88256DE3007B916B/0/2E97F19101D02133C1257B18004D25E9/$file/determination_of_central_anterior_chamber_depth_with_zeiss_sl_120_and_sl_130_slit_lamps_sec.pdf).

By performing slit lamp measurements as suggested by Smith, it is possible to determine the axial position parameter of at least a portion of the anterior surface of the capsular bag. The slit lamp measurements have shown to be more reliable when, prior to performing the measurements, a capsular tension ring has been inserted into the capsular bag.

Additionally or alternatively, the ophthalmic measuring system 21 may comprise a laser scanning microscope for determining interfaces between tissue regions. Such a laser scanning microscope is described for example in document DE 10 2010 010 569 A1. The content of this document is incorporated herein by reference in its entirety.

Additionally or alternatively, the ophthalmic measuring system 21 comprises a gaze tracker and/or a pupil position detection system. The ophthalmic measuring system 21 may comprise one or more further components, which are useful for carrying out cataract surgery. By way of example, the ophthalmic measuring system comprises an illumination system for red reflex illumination and/or surrounding field illumination. Additionally or alternatively, the ophthalmic measuring system 21 may comprise a device for determining the objective refraction of the eye, such as a wavefront aberrometer.

The system 40 may further comprise further measurement units, which neither irradiate the eye with light, nor with ultrasound radiation. Byway of example, the system 40 may comprise a tonometer 23 for determining an intraocular pressure of the eye. It has shown that the selection of the intraocular lens can be performed more reliably, when the measurement of the position parameter of the capsular bag is carried out at a predefined intraocular pressure. The predefined intraocular pressure may be 2666 Pa (i.e. 20 mmHg). Additionally or alternatively, also the preoperative axial length and/or the preoperative refractive power of the cornea, such as the local mean surface refractive power at the corneal apex may be measured when the intraocular pressure is adjusted to the predefined pressure value.

Adjusting the intraocular pressure may be performed by adjusting a height difference between an infusion container and the eye. The infusion container may contain an irrigation fluid. The infusion container may be connected to the eye by a flexible tubing to provide a controlled flow of the irrigation fluid into the anterior chamber of the eye.

During at least a portion of the measurements of the ophthalmic measurement system 21, a capsular tension ring may be contained in the at least partially emptied capsular bag. The capsular tension ring may be configured to form the capsular bag into a substantially flat shape.

The system 40 further comprises a data processing system 24, which comprises a processing unit 25, a data storage system 26 and an input/output unit 27. The input/output unit 27 may comprise a display and/or a device for superimposing the data onto an image viewed by a user of a surgical microscope.

The processing unit 25 is configured to determine, depending on the data, which has been acquired by the ophthalmic measuring system 21, a position parameter and/or a geometrical parameter of a portion of the capsular bag. In particular, the processing unit 25 is configured to determine an axial distance between the cornea and a portion of the anterior surface of the emptied capsular bag, as has been described with reference to FIG. 3.

The processing unit 25 is further configured to determine the selection parameter of the intraocular lens depending on the determined position parameter and/or depending on the geometrical parameter, for example, by applying an equation derived from a regression analysis.

The data storage system stores data of a plurality of intraocular lenses. Depending on the determined selection parameter, the processing unit selects an intraocular lens which best fits the desired optical characteristics. Since the measurement of the position parameter and/or geometrical parameter can be performed during cataract surgery, the data storage system may store information on those intraocular lenses, which are available to be immediately implanted into the patient's eye.

Figure 6:
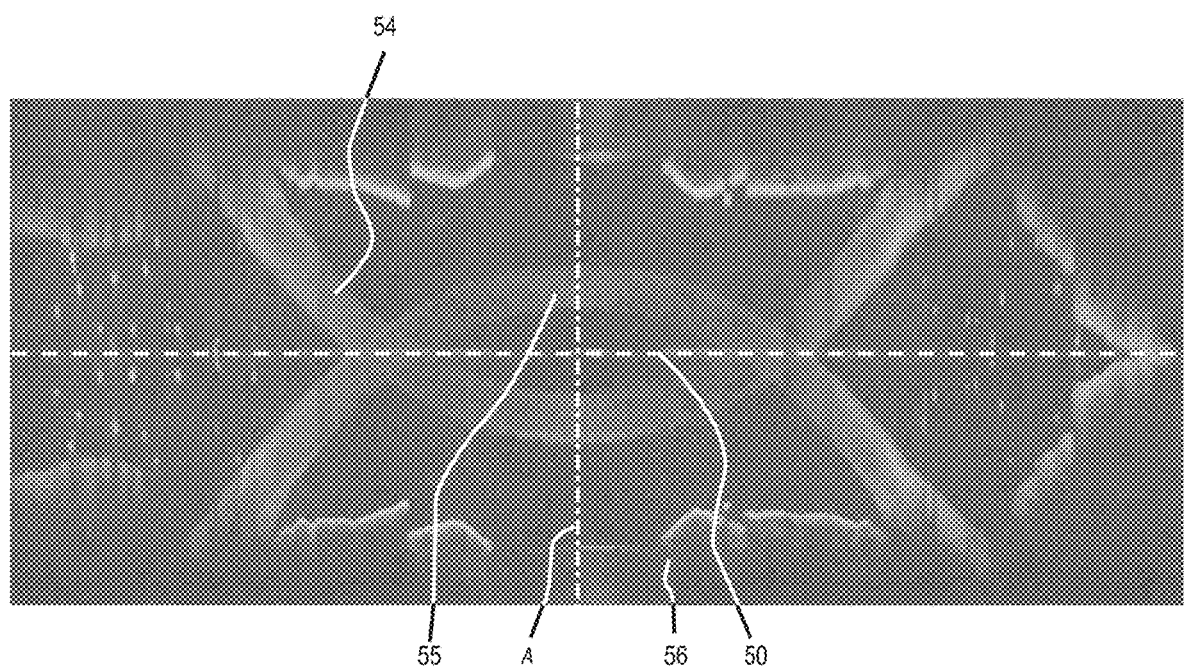
FIG. 6 shows an image of a portion of an anterior segment of the eye acquired by a system according to a second exemplary embodiment.

FIG. 6 shows an exemplary image of an anterior segment of the eye, acquired by a system according to a second exemplary embodiment. In the second exemplary embodiment, the ophthalmic measuring device comprises an FD-OCT system.

Since the spectrum acquired in FD-OCT is a real function, its Fourier transform is symmetrical with respect to the equal path length point. The symmetrical nature of the Fourier transform causes a mirror image which has a slightly degraded resolution, and which is superimposed onto the real image. In conventional techniques of FD-OCT, the measured sample has therefore to be positioned at one side of the axial position of the OCT beam, where the optical path length difference between the measuring arm and the reference arm is zero. Although this allows to avoid overlapping of mirror images, this considerably reduces the axial scanning range to one half.

The line 50 in FIG. 6 indicates the axial position of the OCT beam, where the optical path length difference is zero. The OCT beam has scanned the anterior segment of the eye with a beam axis oriented substantially parallel to the optical axis of the eye. The symmetrical nature of the Fourier transform causes a real image and a mirror image, which are symmetrical with respect to line 50.

The image shown in FIG. 6 has been acquired by setting the axial position 50 of the OCT beam, where the optical path length difference is zero, such that it is located within the anterior chamber where the OCT beam is substantially arranged along the optical axis A of the eye. Thereby, the object is not located at one side of the axial position 50, as in conventional FD-OCT techniques. The image shows structures of the mirror image 54 and structures of the real image 55 which partially overlap.

As can be seen by comparing FIG. 6 with FIG. 3, the axial position parameter of the anterior surface portion of the capsular bag can still be determined with high accuracy, since structures of the mirror image are not superimposed onto structures of the real image, where the apex of the cornea or the capsular bag is located. Thereby, the axial scanning range of the OCT system can be increased, while still allowing to image in a single OCT scan those portions of the eye, which are necessary to determine position parameters of the capsular bag.

Figure 7:
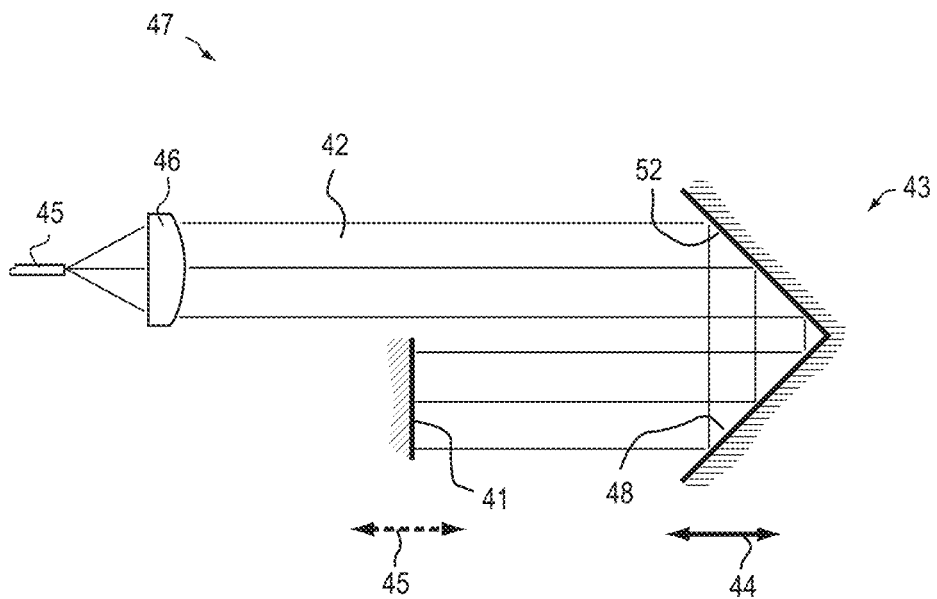
FIG. 7 shows a portion of a reference arm, of a system according to a second exemplary embodiment.

FIG. 7 shows a portion of a system according to a third exemplary embodiment. In the third exemplary embodiment, the ophthalmic measuring system comprises an OCT system, which is configured such that an axial position of an axial scanning range is adjustable. The OCT system of the third exemplary embodiment may be a time domain OCT system and/or a frequency domain OCT system.

In the reference arm 47 of the OCT system, light is emitted from an optical fiber 45 and collimated by a collimating lens 46 to form a substantially parallel beam bundle 42 of reference light, which is reflected at a reference mirror 45. The reference mirror 45 may be configured to be displaceable along an axis of the parallel beam bundle (indicated with dashed arrow 45). When the OCT system is configured as a FD-OCT system, the reference mirror may be configured to be stationary.

In the beam path of the parallel beam bundle 42, an optical path length adjuster 43 is arranged. The optical path length adjuster 43 is configured to adjust the length of the optical path in the reference arm. The length of the optical path is adjustable by adjusting the position of the optical path length adjuster 43. The optical path length adjuster 43 comprises two mirror surfaces 52, 48, which are oriented at 90 degrees relative to each other.

Displacing the position of the optical path length adjuster 43 by an amount of $\Delta x$ in a direction along the axis of the beam bundle 42 (indicated by arrow 44) causes the optical path in the reference arm to be changed by an amount of $2 \cdot \Delta x$. Thereby, the equal path length point in the measuring arm is displaced by an amount of $\Delta x / n_g$ with $n_g$ being the group refractive index of the object in the region within which the equal path length point is displaced by the optical path length adjuster 43. Inside the anterior chamber, the group refractive index $n_g$ may be about 1.36.

This allows to image a portion of an anterior segment of the eye, which ranges from the cornea to the anterior portion of the capsular bag with a plurality of scans, wherein each of the scans has a different position of the optical path length adjuster 43. Thereby, each of the scans has a different axial position of the axial scanning range. The data processing unit is configured to combine these scans e.g. by applying a stitching operation to form a single image.

Additionally or alternatively, the optical beam path adjuster may be arranged in the measuring arm of the OCT system. Additionally or alternatively, the optical measuring system may be configured to be displaceable relative to the eye in a direction along the optical axis of the eye. This also displaces the axial position of the axial scanning range of the OCT system relative to the eye.

Thereby, the OCT system can be efficiently used to acquire data, which allow to determine position parameters of the capsular bag relative to the cornea.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A method of determining at least one selection parameter for selecting an intraocular lens to be inserted into an eye; the method comprising:
   acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;
   reading the data by a data processing system;
   determining a connecting line between two substantially opposing portions of an edge of an opening in the anterior surface, depending on the data;
   determining an axial position parameter, which is representative of the axial position of the outer portion of the anterior surface, depending on the data; and
   determining the at least one selection parameter for selecting the intraocular lens depending on the determined axial position parameter, and further depending on a refractive power of a cornea of the eye.

2. The method of claim 1, further comprising determining a distance line between the connecting line and a central portion of an apex of the eye, depending on the data.

3. The method of claim 2, wherein either:
the distance line is determined so that the distance line and the connecting line intersect at right angles; and/or
the distance line is determined so that it is substantially oriented along the optical axis of the eye.

4. A method of determining at least one selection parameter for selecting an intraocular lens to be inserted into an eye; the method comprising:
acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;
reading the data by a data processing system;
determining an axial position parameter, which is representative of the axial position of the outer portion of the anterior surface, depending on the data; and
determining the at least one selection parameter for selecting the intraocular lens depending on the determined axial position parameter, and further depending on a refractive power of a cornea of the eye, wherein the determining of the at least one selection parameter comprises performing a regression analysis configured to establish a relationship between one or more input variables and one or more output variables;
wherein the input variables of the regression analysis comprise:
an axial length ($AL_{pre}$) of the eye which is measured before the natural lens has been at least partially removed from the capsular bag;
the axial position parameter, which is an axial distance (AD) along the optical axis of the eye between the axial position of the portion of the anterior surface of the at least partially empty capsular bag and an axial position of a central portion of a cornea of the eye, and
a local mean surface refractive power of the cornea ($K_{pre}$), which is defined as $$K_{pre} = \frac{0.332}{2} \cdot \left(\frac{1}{r_1} + \frac{1}{r_2}\right),$$

with $r_1$ and $r_2$ being principal radii of curvature of the cornea, wherein the local mean surface refractive power is measured at the apex of the cornea and before the natural lens (2) has been at least partially removed from the capsular bag.

5. The method of claim 4, wherein the regression analysis is performed for determining the constants $c_0$, $c_1$, $c_2$, and $c_3$ in the following equation:

$$P_{IOL} = c_0 + c_1 \cdot AL_{pre} + c_2 \cdot K_{pre} + c_3 \cdot AD,$$

wherein $P_{IOL}$ is the optical power of the intraocular lens.

6. A method of determining at least one selection parameter for selecting an intraocular lens to be inserted into an eye; the method comprising:
acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;
reading the data by a data processing system;
determining an axial position parameter, which is representative of the axial position of the outer portion of the anterior surface, depending on the data; and
determining the at least one selection parameter for selecting the intraocular lens depending on the determined axial position parameter, and further depending on a refractive power of a cornea of the eye,
wherein the determining of the at least one selection parameter comprises performing a regression analysis for determining constants of an equation wherein the equation has not more than three input variables which are used in the regression analysis and one or more output variables which are used in the regression analysis;
wherein the three input variables are:
a first input variable which is determined depending on the axial position parameter;
a second input variable which is an axial length of the eye; and
a third input variable which is a refractive power of the cornea,
wherein the refractive power of the cornea is a local mean surface refractive power of the cornea.

7. The method of claim 6, wherein the local mean surface refractive power ($K_{pre}$) of the cornea is defined as $$K_{pre} = \frac{0.332}{2} \cdot \left(\frac{1}{r_1} + \frac{1}{r_2}\right),$$

with $r_1$ and $r_2$ being principal radii of curvature of the cornea.

8. A method of determining at least one selection parameter for selecting an intraocular lens to be inserted into an eye; the method comprising:
acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;
reading the data by a data processing system;
determining an axial position parameter, which is representative of the axial position of the outer portion of the anterior surface, depending on the data; and
determining the at least one selection parameter for selecting the intraocular lens depending on the determined axial position parameter, and further depending on a refractive power of a cornea of the eye, wherein the at least one selection parameter is further determined depending on a local mean surface refractive power of the cornea ($K_{pre}$), which is defined as $$K_{pre} = \frac{0.332}{2} \cdot \left(\frac{1}{r_1} + \frac{1}{r_2}\right),$$

with $r_1$ and $r_2$ being principal radii of curvature of the cornea.

9. A method of determining at least one selection parameter for selecting an intraocular lens to be inserted into an eye; the method comprising:

acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;

reading the data by a data processing system;

determining an axial position parameter, which is representative of the axial position of the outer portion of the anterior surface, depending on the data; and determining the at least one selection parameter for selecting the intraocular lens depending on the determined axial position parameter, and further depending on a refractive power of a cornea of the eye, wherein the determining of the at least one selection parameter comprises performing a regression analysis for determining constants of an equation wherein the equation has not more than three input variables which are used in the regression analysis and one or more output variables which are used in the regression analysis;

wherein the three input variables are:

a first input variable which is determined depending on the axial position parameter; and a second input variable which is an axial length of the eye; and a third input variable, which is a central cornea thickness, wherein the one or more output variables comprise a predicted postoperative chamber depth, wherein the regression analysis is performed for determining the constants $a_0$, $a_1$, and $a_2$ in the following equation:

$$ACD_{postOP} = a_0 + a_1 \cdot (AD + CCT) + a_2 \cdot AL_{pre},$$

wherein:

AD denotes the axial position parameter;

CCT denotes the central cornea thickness;

$AL_{pre}$ denotes the axial length of the eye; and $ACD_{postOP}$ denotes the predicted postoperative anterior chamber depth.

10. A method of determining at least one selection parameter for selecting an intraocular lens to be inserted into an eye; the method comprising:

acquiring, by an optical coherence tomography (OCT) system, OCT data indicative of an axial position of at least an outer portion of an anterior surface of an at least partially empty capsular bag of the eye, relative to an optical axis of the eye, wherein the data are acquired after a natural lens of the eye has been at least partially removed from the capsular bag;

reading the data by a data processing system;

determining an axial position parameter, which is representative of the axial position of the outer portion of the anterior surface, depending on the data; and determining the at least one selection parameter for selecting the intraocular lens depending on the determined axial position parameter, and further depending on a refractive power of a cornea of the eye, further comprising determining a connecting line between two portions of an edge of an opening in the anterior surface, depending on the data.

* * * * *

UNITED STATES PATENT AND TRADEMARK OFFICE
CERTIFICATE OF CORRECTION

PATENT NO. : 10,736,503 B2  
APPLICATION NO. : 16/034462  
DATED : August 11, 2020  
INVENTOR(S) : Marco Wilzbach et al.

Page 1 of 1

It is certified that error appears in the above-identified patent and that said Letters Patent is hereby corrected as shown below:

In the Specification

Column 12, Line 49, "$c_2=-36$" should read --$c_2=-3.6$--

Signed and Sealed this  
Twenty-fourth Day of November, 2020

Andrei Iancu  
*Director of the United States Patent and Trademark Office*